(12) United States Patent
Westenbrink

(10) Patent No.: US 11,660,382 B2
(45) Date of Patent: May 30, 2023

(54) VALVE LEAK DETECTION SYSTEM

(71) Applicant: Quanta Dialysis Technologies Limited, Warwickshire (GB)

(72) Inventor: Eric William Westenbrink, Warwickshire (GB)

(73) Assignee: Quanta Dialysis Technologies Limited, Warwickshire (GB)

( * ) Notice: Subject to any disclaimer, the term of this patent is extended or adjusted under 35 U.S.C. 154(b) by 82 days.

(21) Appl. No.: 16/472,656

(22) PCT Filed: Dec. 13, 2017

(86) PCT No.: PCT/GB2017/053738
§ 371 (c)(1),
(2) Date: Jun. 21, 2019

(87) PCT Pub. No.: WO2018/115816
PCT Pub. Date: Jun. 28, 2018

(65) Prior Publication Data
US 2019/0358381 A1 Nov. 28, 2019

(30) Foreign Application Priority Data
Dec. 23, 2016 (GB) ...................................... 1622119

(51) Int. Cl.
*A61M 1/36* (2006.01)
*A61M 60/268* (2021.01)
(Continued)

(52) U.S. Cl.
CPC .......... *A61M 1/367* (2013.01); *A61M 60/113* (2021.01); *A61M 60/268* (2021.01);
(Continued)

(58) Field of Classification Search
CPC ................ A61M 1/1037; A61M 1/367; A61M 2205/128; A61M 2205/15;
(Continued)

(56) References Cited

U.S. PATENT DOCUMENTS 2,696,173 A 12/1954 Thormod
3,468,261 A 9/1969 Schmierer
(Continued)

FOREIGN PATENT DOCUMENTS

CA 81430 8/1997
DE 10024447 A1 11/2001
(Continued)

OTHER PUBLICATIONS

US 8,793,908 B2, 08/2014, Bourdeaut (withdrawn)
(Continued)

*Primary Examiner* — Patrick Orme
(74) *Attorney, Agent, or Firm* — Cooley LLP

(57) ABSTRACT

An improved valve leak detection system. The improved valve leak detection system comprises a membrane pump defining a flow path arranged to be opened and closed by at least one valve, a measuring device, a comparator, and a signal generator. The measuring device is configured to determine a conductivity value between two points on the flow path of the membrane pump, one point arranged upstream of the at least one valve and the other point arranged downstream of the at least one valve. The measuring device measures the conductivity value when the at least one valve is closed. The comparator is configured to continuously monitor the conductivity value. The signal generator is arranged to provide an output signal when the conductivity value is indicative of a valve leak condition for a set number of measurements within a set period of time.

15 Claims, 9 Drawing Sheets

(51) Int. Cl.
  *A61M 60/851* (2021.01)
  *A61M 60/849* (2021.01)
  *A61M 60/113* (2021.01)
  *A61M 60/562* (2021.01)
  *A61M 60/427* (2021.01)
  *A61M 60/37* (2021.01)
  *A61M 60/837* (2021.01)

(52) U.S. Cl.
  CPC .......... *A61M 60/37* (2021.01); *A61M 60/427* (2021.01); *A61M 60/562* (2021.01); *A61M 60/837* (2021.01); *A61M 60/849* (2021.01); *A61M 60/851* (2021.01); *A61M 2205/128* (2013.01); *A61M 2205/15* (2013.01); *A61M 2205/273* (2013.01); *A61M 2205/702* (2013.01)

(58) Field of Classification Search
  CPC ...... A61M 2205/273; A61M 2205/702; A61M 60/268; F04B 51/00; F04B 2201/0605
  See application file for complete search history.

(56) References Cited

U.S. PATENT DOCUMENTS

| | | | |
|---|---|---|---|
| 3,605,566 | A | 9/1971 | Vetter |
| 3,606,592 | A | 9/1971 | Madurski et al. |
| 3,753,493 | A | 6/1973 | Mellor |
| 3,774,762 | A | 11/1973 | Lichtenstein |
| 3,807,906 | A | 4/1974 | Breit |
| 3,921,622 | A | 11/1975 | Cole |
| 3,972,320 | A | 6/1976 | Kalman |
| 4,070,725 | A | 1/1978 | Cornelius |
| 4,142,845 | A | 3/1979 | Lepp et al. |
| 4,161,264 | A | 7/1979 | Malmgren |
| 4,205,686 | A | 6/1980 | Harris et al. |
| 4,353,990 | A | 10/1982 | Manske et al. |
| 4,366,061 | A | 12/1982 | Papanek et al. |
| 4,368,261 | A | 1/1983 | Klose |
| 4,370,983 | A | 2/1983 | Lichtenstein |
| 4,430,048 | A | 2/1984 | Fritsch |
| 4,494,912 | A | 1/1985 | Paullukonis |
| D277,991 | S | 3/1985 | Becker |
| 4,534,755 | A | 8/1985 | Calvert et al. |
| 4,534,756 | A | 8/1985 | Nelson |
| 4,546,669 | A | 10/1985 | Fischer et al. |
| 4,564,342 | A | 1/1986 | Weber et al. |
| 4,599,165 | A | 7/1986 | Chevallet |
| 4,648,869 | A | 3/1987 | Bobo, Jr. |
| 4,666,598 | A | 5/1987 | Heath et al. |
| 3,338,171 | A | 8/1987 | Conklin et al. |
| 4,710,163 | A | 12/1987 | Butterfield |
| 4,771,792 | A | 9/1988 | Seale |
| 4,828,543 | A | 5/1989 | Weiss et al. |
| 4,897,184 | A | 1/1990 | Shouldice et al. |
| D308,249 | S | 5/1990 | Buckley |
| 4,969,991 | A | 11/1990 | Valadez |
| 5,000,664 | A * | 3/1991 | Lawless ............ A61M 5/16831 417/63 |
| 5,012,197 | A | 4/1991 | Seiffert et al. |
| 5,032,265 | A | 7/1991 | Jha et al. |
| 5,055,198 | A | 10/1991 | Shettigar |
| 5,095,910 | A | 3/1992 | Powers |
| 5,103,211 | A | 4/1992 | Daoud et al. |
| 5,126,831 | A | 6/1992 | Nakagawara |
| 5,232,434 | A | 8/1993 | Inagaki et al. |
| 5,252,213 | A | 10/1993 | Ahmad et al. |
| D341,890 | S | 11/1993 | Sievert et al. |
| D344,339 | S | 2/1994 | Yoshikawa et al. |
| 5,304,349 | A | 4/1994 | Polaschegg |
| D347,896 | S | 6/1994 | Dickinson et al. |
| D351,470 | S | 10/1994 | Scherer et al. |
| 5,385,540 | A | 1/1995 | Abbott et al. |
| 5,421,823 | A | 6/1995 | Kamen et al. |
| 5,458,468 | A | 10/1995 | Ye et al. |
| 5,476,368 | A | 12/1995 | Rabenau et al. |
| 5,476,792 | A | 12/1995 | Ezrielev et al. |
| D370,979 | S | 6/1996 | Pascale et al. |
| 5,558,347 | A | 9/1996 | Nicholson |
| 5,586,872 | A | 12/1996 | Skobelev et al. |
| 5,586,873 | A | 12/1996 | Novak et al. |
| 5,591,344 | A | 1/1997 | Kenley et al. |
| 5,643,201 | A | 7/1997 | Peabody et al. |
| 5,650,071 | A | 7/1997 | Brugger et al. |
| 5,653,456 | A | 8/1997 | Mough |
| 5,658,456 | A | 8/1997 | Kenley et al. |
| 5,665,307 | A | 9/1997 | Kirschner et al. |
| 5,727,550 | A | 3/1998 | Montecalvo |
| D395,085 | S | 6/1998 | Kenley et al. |
| 5,788,851 | A | 8/1998 | Kenley et al. |
| 5,807,322 | A | 9/1998 | Lindsey et al. |
| 5,882,300 | A | 3/1999 | Malinouskas et al. |
| 5,948,247 | A | 9/1999 | Gillerfalk et al. |
| 5,957,670 | A | 9/1999 | Duncan et al. |
| 5,995,910 | A | 11/1999 | Discenzo |
| 6,077,443 | A | 6/2000 | Goldau |
| 6,126,831 | A | 10/2000 | Goldau et al. |
| 6,132,378 | A | 10/2000 | Marino |
| 6,143,181 | A | 11/2000 | Falkvall et al. |
| 6,153,102 | A | 11/2000 | Kenley et al. |
| 6,216,029 | B1 | 4/2001 | Paltieli |
| 6,218,329 | B1 | 4/2001 | Singh et al. |
| 6,251,279 | B1 | 6/2001 | Peterson et al. |
| 6,261,065 | B1 | 7/2001 | Nayak et al. |
| 6,303,036 | B1 | 10/2001 | Collins et al. |
| 6,382,923 | B1 | 5/2002 | Gray |
| 6,514,462 | B1 | 2/2003 | Simons |
| 6,558,347 | B1 | 5/2003 | Jhuboo et al. |
| 6,582,206 | B2 | 6/2003 | Schluecker |
| 6,626,832 | B1 | 9/2003 | Paltieli et al. |
| 6,626,878 | B1 | 9/2003 | Leisner et al. |
| 6,645,176 | B1 | 11/2003 | Christenson et al. |
| 6,663,829 | B1 | 12/2003 | Kjellstrand |
| 6,733,476 | B2 | 5/2004 | Christenson et al. |
| 6,743,204 | B2 | 6/2004 | Christenson et al. |
| 6,801,646 | B1 | 10/2004 | Pena et al. |
| 6,814,547 | B2 | 11/2004 | Childers et al. |
| 6,967,002 | B1 | 11/2005 | Edgson et al. |
| 7,040,142 | B2 | 5/2006 | Burbank |
| 7,107,837 | B2 | 9/2006 | Lauman et al. |
| 7,153,286 | B2 | 12/2006 | Busby et al. |
| 7,284,964 | B2 | 10/2007 | McDowell et al. |
| 7,434,312 | B2 | 10/2008 | Christenson et al. |
| 7,494,590 | B2 | 2/2009 | Felding et al. |
| 7,648,627 | B2 | 1/2010 | Beden et al. |
| 7,857,976 | B2 | 12/2010 | Bissier et al. |
| 7,874,999 | B2 | 1/2011 | Busby |
| 7,896,197 | B2 | 3/2011 | Furey et al. |
| D641,882 | S | 7/2011 | Hickey et al. |
| 8,114,043 | B2 | 2/2012 | Muller |
| 8,132,368 | B2 | 3/2012 | Nagy et al. |
| 8,137,184 | B2 | 3/2012 | Ajiro et al. |
| 8,137,300 | B2 | 3/2012 | Han et al. |
| 8,167,431 | B2 | 5/2012 | DeCusatis et al. |
| 8,187,184 | B2 | 5/2012 | Muller et al. |
| 8,192,388 | B2 | 6/2012 | Hogard |
| 8,197,431 | B2 | 6/2012 | Bennison |
| 8,221,320 | B2 | 7/2012 | Bouton |
| 8,348,850 | B2 | 1/2013 | Frinak et al. |
| 8,360,977 | B2 | 1/2013 | Marttila et al. |
| 8,529,490 | B2 | 9/2013 | Wariar et al. |
| 8,535,522 | B2 | 9/2013 | Fulkerson et al. |
| 8,535,525 | B2 | 9/2013 | Heyes et al. |
| D693,469 | S | 11/2013 | Chung et al. |
| 8,597,505 | B2 | 12/2013 | Fulkerson et al. |
| D702,842 | S | 4/2014 | Hyde et al. |
| 8,685,244 | B2 | 4/2014 | Heyes et al. |
| 8,696,571 | B2 | 4/2014 | Marttiia et al. |
| 8,708,908 | B2 | 4/2014 | Bouton |
| 8,708,946 | B2 | 4/2014 | Han et al. |
| D705,432 | S | 5/2014 | Lura et al. |
| 8,801,646 | B2 | 8/2014 | Han et al. |
| D714,454 | S | 9/2014 | Amemiya et al. |

(56) References Cited

U.S. PATENT DOCUMENTS

| | | |
|---|---|---|
| D714,946 S | 10/2014 | Lura et al. |
| 8,926,544 B2 | 1/2015 | Hogard et al. |
| D724,740 S | 3/2015 | Collins et al. |
| 8,974,394 B2 | 3/2015 | Frinak et al. |
| 9,011,334 B2 | 4/2015 | Bouton |
| D735,868 S | 8/2015 | Mareguddi et al. |
| 9,220,825 B2 | 12/2015 | Buckberry |
| D781,410 S | 3/2017 | Ritter et al. |
| 9,744,285 B2 | 8/2017 | Heyes et al. |
| 9,833,553 B2 | 12/2017 | Higgitt et al. |
| 10,456,516 B2 | 10/2019 | Heyes et al. |
| D867,597 S | 11/2019 | Bauer et al. |
| 10,543,305 B2 | 1/2020 | Buckberry et al. |
| D879,967 S | 3/2020 | Verguldi et al. |
| D907,211 S | 1/2021 | Spurling |
| 10,881,775 B2 | 1/2021 | Wallace |
| 10,960,120 B2 | 3/2021 | Wallace et al. |
| D924,410 S | 7/2021 | Mendoza et al. |
| D938,046 S | 12/2021 | Gupta et al. |
| 11,365,728 B2 | 6/2022 | Westenbrink |
| 2003/0217962 A1 | 11/2003 | Childers et al. |
| 2004/0195157 A1 | 10/2004 | Mullins et al. |
| 2004/0206703 A1 | 10/2004 | Bosetto et al. |
| 2004/0215129 A1 | 10/2004 | Edgson et al. |
| 2004/0223857 A1 | 11/2004 | Kline |
| 2005/0020961 A1 | 1/2005 | Burbank et al. |
| 2005/0205476 A1 | 9/2005 | Chevallet et al. |
| 2005/0209547 A1 | 9/2005 | Burbank et al. |
| 2005/0234384 A1 | 10/2005 | Westberg et al. |
| 2006/0121623 A1 | 6/2006 | He et al. |
| 2007/0083193 A1 | 4/2007 | Werneth et al. |
| 2008/0200865 A1 | 8/2008 | Bedingfield |
| 2008/0283096 A1 | 11/2008 | Scheringer et al. |
| 2009/0007642 A1 | 1/2009 | Busby et al. |
| 2009/0009290 A1 | 1/2009 | Kneip et al. |
| 2009/0012450 A1 | 1/2009 | Shah et al. |
| 2009/0012452 A1 | 1/2009 | Slepicka et al. |
| 2009/0012457 A1 | 1/2009 | Childers et al. |
| 2009/0101550 A1 | 4/2009 | Muller et al. |
| 2009/0211975 A1 | 8/2009 | Brugger et al. |
| 2009/0230043 A1 | 9/2009 | Heyes et al. |
| 2010/0043694 A1 | 2/2010 | Patel |
| 2010/0045471 A1* | 2/2010 | Meyers .............. G05D 7/0617 340/605 |
| 2010/0089807 A1 | 4/2010 | Heyes et al. |
| 2010/0139254 A1* | 6/2010 | Sebestyen .............. F01N 11/00 60/286 |
| 2010/0263687 A1 | 10/2010 | Braun et al. |
| 2011/0009797 A1 | 1/2011 | Kelly et al. |
| 2011/0034850 A1 | 2/2011 | Jonsson |
| 2011/0132838 A1 | 6/2011 | Curtis et al. |
| 2011/0168614 A1 | 7/2011 | Pouchoulin et al. |
| 2012/0164022 A1 | 6/2012 | Muginstein et al. |
| 2012/0269907 A1 | 10/2012 | Coates |
| 2012/0276549 A1 | 11/2012 | Cunningham et al. |
| 2012/0292237 A1 | 11/2012 | Heyes et al. |
| 2012/0308431 A1 | 12/2012 | Kotsos et al. |
| 2013/0056419 A1 | 3/2013 | Curtis |
| 2013/0153495 A1 | 6/2013 | Kelly et al. |
| 2013/0199998 A1 | 8/2013 | Kelly et al. |
| 2013/0274642 A1 | 10/2013 | Soykan et al. |
| 2014/0224736 A1 | 8/2014 | Heide |
| 2014/0251885 A1 | 9/2014 | Heyes |
| 2014/0299544 A1 | 10/2014 | Wilt et al. |
| 2015/0027951 A1 | 1/2015 | Wallace et al. |
| 2015/0076053 A1 | 3/2015 | Higgitt et al. |
| 2015/0112119 A1 | 4/2015 | Buckberry |
| 2015/0129481 A1 | 5/2015 | Higgitt et al. |
| 2015/0238673 A1 | 8/2015 | Gerber et al. |
| 2015/0258263 A1 | 9/2015 | Hogard |
| 2015/0352269 A1 | 12/2015 | Gerber et al. |
| 2015/0359954 A1 | 12/2015 | Gerber et al. |
| 2016/0045656 A1 | 2/2016 | Buckberry |
| 2016/0051743 A1 | 2/2016 | Buckberry |
| 2016/0058933 A1 | 3/2016 | Ballantyne et al. |
| 2016/0077644 A1 | 3/2016 | Ritter et al. |
| 2017/0056576 A1 | 3/2017 | Doyle et al. |
| 2017/0167983 A1 | 6/2017 | Klomp et al. |
| 2017/0252498 A1 | 9/2017 | Heyes et al. |
| 2017/0296730 A1 | 10/2017 | Soto et al. |
| 2018/0133391 A1 | 5/2018 | Heyes et al. |
| 2018/0154059 A1 | 6/2018 | Heyes et al. |
| 2018/0193545 A1 | 7/2018 | Crnkovich et al. |
| 2018/0344915 A1 | 12/2018 | Wallace |
| 2019/0001042 A1 | 1/2019 | Buckberry |
| 2019/0015577 A1 | 1/2019 | Garrido et al. |
| 2019/0024654 A1 | 1/2019 | May et al. |
| 2019/0374698 A1 | 12/2019 | Buckberry et al. |
| 2019/0376504 A1 | 12/2019 | Westenbrink |
| 2019/0385434 A1 | 12/2019 | Yuds et al. |
| 2020/0030515 A1 | 1/2020 | Merchant |
| 2020/0075159 A1 | 3/2020 | Bardorz et al. |
| 2020/0268958 A1 | 8/2020 | Heyes et al. |
| 2020/0276372 A1 | 9/2020 | Milad et al. |
| 2020/0330671 A1 | 10/2020 | Buckberry et al. |
| 2022/0001087 A1 | 1/2022 | Heyes et al. |

FOREIGN PATENT DOCUMENTS

| | | |
|---|---|---|
| EM | 004375764-0001 | 10/2017 |
| EM | 004375764-0002 | 10/2017 |
| EP | 0165751 A2 | 12/1985 |
| EP | 0754468 A2 | 1/1997 |
| EP | 2219703 A1 | 8/2010 |
| EP | 2955512 A1 | 12/2015 |
| FR | 2310136 | 12/1976 |
| GB | 9007955125-0001 | 5/2020 |
| GB | 9007955125-0002 | 5/2020 |
| JP | H04266740 | 9/1992 |
| JP | H06261872 | 9/1994 |
| JP | H07174659 | 7/1995 |
| JP | 2000/130334 | 5/2000 |
| JP | D1645323 | 11/2020 |
| WO | WO 81/01800 | 7/1981 |
| WO | WO 91/00113 | 1/1991 |
| WO | WO 91/16542 | 10/1991 |
| WO | WO 95/06205 | 3/1995 |
| WO | WO 95/25893 | 9/1995 |
| WO | WO 96/25214 | 8/1996 |
| WO | WO 97/10013 | 3/1997 |
| WO | WO 97/28368 | 8/1997 |
| WO | WO 99/29356 | 6/1999 |
| WO | WO 2000/006217 | 2/2000 |
| WO | WO 00/57935 | 10/2000 |
| WO | WO 02/066833 | 8/2002 |
| WO | WO 02/081917 | 10/2002 |
| WO | WO 2003/101510 | 12/2003 |
| WO | WO 2005/044339 | 5/2005 |
| WO | WO 2005/080794 | 9/2005 |
| WO | WO 2006/120415 | 11/2006 |
| WO | WO 2006/120417 | 11/2006 |
| WO | WO 2008/100671 | 8/2008 |
| WO | WO 2008/106191 | 9/2008 |
| WO | WO 2008/135245 | 11/2008 |
| WO | WO 2009/006489 | 1/2009 |
| WO | WO 2009/024333 | 2/2009 |
| WO | WO 2009/038834 | 3/2009 |
| WO | 2009061608 A1 | 5/2009 |
| WO | WO 2009/127624 | 10/2009 |
| WO | WO 2010/089130 | 8/2010 |
| WO | WO 2010/146343 | 12/2010 |
| WO | WO 2011/027118 | 3/2011 |
| WO | WO 2011/068885 | 6/2011 |
| WO | WO 2011/105697 | 9/2011 |
| WO | WO 2011/105698 | 9/2011 |
| WO | WO 2013/052680 | 4/2013 |
| WO | WO 2013/057109 | 4/2013 |
| WO | WO 2013/110906 | 8/2013 |
| WO | WO 2013/110919 | 8/2013 |
| WO | WO 2013/114063 | 8/2013 |
| WO | WO 2013/121162 | 8/2013 |
| WO | WO 2013/121163 | 8/2013 |
| WO | WO 2014/072195 | 5/2014 |
| WO | WO 2014/082855 | 6/2014 |

(56) References Cited

FOREIGN PATENT DOCUMENTS

| WO | WO 2014/155121 | 10/2014 |
|---|---|---|
| WO | WO 2015/007596 | 1/2015 |
| WO | WO 2015/022537 | 2/2015 |
| WO | WO 2016/016870 | 2/2016 |
| WO | WO 2017/137723 | 8/2017 |
| WO | WO 2018/115816 | 6/2018 |

OTHER PUBLICATIONS

International Search Report and Written Opinion for International Application No. PCT/GB2017/0537738 dated Feb. 27, 2018.
He et al., "A Fluorescent Sensor with High Selectivity and Sensitivity for Potassium in Water," Journal of the American Chemical Society 2003 125 (6), 1468-1469.
Kivi, Air Embolism, Healthline, Aug. 20, 2012, p. 1-5.
Ergo-Express Motorized Dialysis Cart, Aug. 14, 2017, youtube.com [online], Available from internet, URL: <https://www.youtube.com/watch?v=j4rAXthOmbY> (Year: 2017).
Home Dialysis Tescon Aqua Tech, Aug. 1, 2020, youtube.com [online], Available from internet, URL: <https://www.youtube.com/watch?v=WLLPZoS mz4> (Year: 2020).
LHO2028 Portable Hemodialysis Machine, date unknown, aliexpress.com [online], Available from internet: <https://www.aliexpress.com/item/1005003324875329.html?randl_currency=USD&_randl_shipto=US&src=google&afffcid=1003bab3b8db4e93b9ba88522a14cfc1-1641319351626-05232-UneMJZVf&aff_fsk=UneMJZVf&aff_platform±aaf&sk=UneMJZVf&aff_trace_key= (Year: 2022).
Medical Hemodialysis Machine, date unknown, aliexpress.com [online], Available from internet: <https://www.aliexpress.com/item/1005003445721549.html?_randl_currency=USD&_randl_shipto=US&src=google&aff_fcid-a524f3f9cd9b4976b6b47962f3439d62-1641319166409-02691-UneMJZVf&aff_fsk=UneMJZVf&aff_platform=aaf&sk=UneMJZVf&aff_trace_key=a524f3f9cd9b4976b6b47962f3439d62-1641319166409-02691-UneMJZVf&terminal_id=d0c2cca4b7664d128cb4801 a9ef03ff2> (Year: 2022).
Millenium HX Portable Dialysis Water System, Jul. 2, 2014, youtube.com [online], Available from internet, URL: <https://www.youtube.com/watch?v=IGEbPi2CDsw>(Year:2014).
Portable home dialysis device, Nov. 2, 2017, med-technews.com [online], Available from internet: <https://www.med-technews.com/news/portable-home-dialysis-device-to-launch-next-year/ (Year: 2017).

* cited by examiner

VALVE LEAK DETECTION SYSTEM

This application is a National Stage Entry entitled to and hereby claiming priority under 35 U.S.C. §§ 365 and 371 to corresponding PCT Application No. PCT/GB2017/053738, filed Dec. 13, 2017 entitled "Improved Valve Leak Detection System", which in turn claims priority to G.B. Patent Application No.: 1622119.4, filed Dec. 23, 2016, entitled the same. The disclosures of the above applications are incorporated herein by reference in their entireties.

The present invention relates to an improved valve leak detection system.

Fluid pumps, for example blood pumps for the extracorporeal circulation of blood are used in a number of medical applications, for example in hemodialysis, and haemodiafiltration.

In hemodialysis machines, it is known to use a disposable cartridge comprising a rigid frame defining fluid pathways and chambers and a flexible membrane covering a surface of the cartridge. The cartridge is loaded into a hemodialysis machine, where pressure, typically pneumatic pressure, exerted on the outside surface of the flexible membrane, causes the membrane to move back and forth. This back and forth action in the region of a chamber acts as a fluid pump, which is thus often referred to as a membrane pump. Such a machine is disclosed in WO 2013/121163, the contents thereof are hereby incorporated by reference.

The movement of the flexible membrane may also be used to mix two or more fluids in a chamber, such as bicarbonate and acid to create dialysate.

The movement of the flexible membrane may also be used to open and close valves defined in the rigid frame of the disposable cartridge. Such a system is disclosed in WO 2013/110919, the contents thereof are hereby incorporated by reference.

Because of its use in hemodialysis, in pumping and mixing fluids, the cartridge may be referred to as a haemodialysis pulsatile pumping cartridge. Such a cartridge is typically made of a rigid frame of polyethylene and a flexible membrane of polyvinyl chloride (PVC).

In use, the cartridge is loaded in a hemodialysis machine and undergoes repeated deformations in the localised regions of the pump chambers, mixing chambers and valves. In a typical cycle, the machine will perform a priming stage, a treatment stage, including flow balance and ultrafiltration stages following by a purge stage.

Such a dialysis machine relies on volumetric control. Dosing and mixing of fluids is controlled by the volume of the pump chambers which in turn is affected by the flexibility of the membrane. The specific flexibility of the membrane is therefore essential to the accurate running of the dialysis machine. Similarly, the flow of fluids into and out of the pump chambers is controlled by inlet and outlet valves. The inlet and outlet valves rely on the deformation of the flexible membrane to accurately control fluid flow.

Repeated deformations gradually cause plastic deformation of the flexible membrane. Thus the cartridges may be engineered to withstand a specific cycle loading, along with a reserve factor. Once used, the cartridge is disposed of and should not be used again. Such a cartridge is termed a disposable cartridge, given its limited lifespan, relative to the dialysis machine.

Re-use of a disposable cartridge designed for a single cycle, or re-use of a disposable cartridge designed for a specific number of cycles, beyond that number of cycles, may reduce the efficacy of treatment and has the potential to cause damage to the dialysis machine.

Given the typical make-up of the disposable cartridge, and that a typical cycle ends with a purge stage that washes and empties the disposable cartridge to remove any residual fluids, a used disposable cartridge does not visibly show any distinct features, as compared to an unused disposable cartridge. Therefore there is a risk of disposable cartridge re-use, either deliberate or accidental.

Valve leak systems are installed in the dialysis machine to detect if any of the valves on the disposable cartridge are not closing properly, such that there is a leak of fluid through the valve. The valve leak system comprises first and second conductivity electrodes arranged upstream and downstream of the valve respectively. A conductivity measurement is taken across the electrodes when the valve is closed. For a normally functioning valve, a relatively low conductivity will be detected when the valve is closed. If a valve is leaking however, a relatively high conductivity is detected, as the leaking fluid carries the charge through the valve, between the first and second conductivity electrodes.

However, environmental factors, such as degassing in the dialysate fluid mixture, may interfere with the accuracy of known valve leak detection systems.

The present invention aims to provide an improved valve leak detection system.

According to an aspect of the present invention, there is provided a valve leak detection system comprising a membrane pump defining a flow path arranged to be opened and closed by at least one valve, a measuring device; a comparator; and a signal generator, wherein the measuring device is configured to determine a conductivity value between a first point and a second point on the flow path of the membrane pump, the first point being arranged upstream of the at least one valve and the second point being arranged downstream of the at least one valve, whereby the measuring device measures the conductivity value when the at least one valve is closed, wherein the comparator is configured to continuously monitor the conductivity value, and the signal generator is arranged to provide an output signal when the conductivity value is indicative of a valve leak condition for a set number of measurements within a predetermined window.

According to another aspect of the present invention, there is provided a valve leak detection system comprising a membrane pump defining a flow path arranged to be opened and closed by at least one valve, a measuring device; a comparator; and a signal generator, wherein the measuring device is configured to determine a conductivity value between a first point and a second point on the flow path of the membrane pump, the first point being arranged upstream of the at least one valve and the second point being arranged downstream of the at least one valve, whereby the measuring device measures the conductivity value when the at least one valve is closed, wherein the comparator is configured to continuously monitor the conductivity value, and the signal generator is arranged to provide an output signal when the conductivity value is indicative of a valve leak condition for a set number of measurements within a set period of time.

By monitoring the conductivity value for a set number of times, temporary spikes due to irregularities such as air in the system may be discounted to prevent false valve leak detection readings.

The set period of time may be a moving time window. This allows continuous monitoring of the valves. The time window may be set as between 1 minute and 60 minutes, or preferably, between 2 minutes and 15 minutes, or most preferably as 5 minutes.

According to yet a further aspect of the invention, there is provided a valve leak detection system comprising a membrane pump defining a flow path arranged to be opened and closed by at least one valve, a measuring device; a comparator; and a signal generator, wherein the measuring device is configured to determine a conductivity value between a first point and a second point on the flow path of the membrane pump, the first point being arranged upstream of the at least one valve and the second point being arranged downstream of the at least one valve, whereby the measuring device measures the conductivity value when the at least one valve is closed, wherein the comparator is configured to continuously monitor the conductivity value, and the signal generator is arranged to provide an output signal when the conductivity value is indicative of a valve leak condition for a set number of measurements within a set number of valve operations.

This provides a valve leak detection system with the same sensitivity no matter how often the valve is being operated.

The valve leak detection system may rely on a combination of a moving time window and a set number of valve operations.

The conductivity value may be determined by taking measurements of the frequency of an oscillating voltage applied across the measuring device. Thus the conductivity value is measured using frequency.

The comparator may measure the difference between the minimum and maximum conductivity value measured within a single pump cycle to detect a variation in the conductivity value. This removes the oscillatory nature of the data.

The comparator may compare the variation in the conductivity value with a pre-determined threshold value. The threshold value may be chosen in order to determine the sensitivity of the valve leak detection system. Alternatively, or additionally, the comparator may compare the variation in the conductivity value with a dynamic threshold value. The dynamic threshold value allows the valve leak detection system to be tuned to the different stages of a typical cycle of the dialysis machine.

By comparing the variation in the conductivity value with a threshold value, valve leak may be identified.

The output signal may be provided when the variation in the conductivity value is above the threshold value. This alerts the patient or dialysis machine operator to the detection of a valve leak.

The detection system may further comprise a processor arranged to receive the output signal. The output signal may be stored in the processor. Thus further analysis may be performed on the identified characteristic. Patterns of deliberate or accidental cartridge re-use may then be monitored.

The membrane pump may be provided on a cartridge.

The measuring device may be a pair of electrodes. Alternatively the measuring device may be a pair of capacitance probes.

The membrane pump may be arranged to be opened and closed by two valves, a first valve arranged upstream of the membrane pump and a second valve arranged downstream of the membrane pump, and wherein the first point is arranged upstream of the first valve and the second point is arranged downstream of the second valve.

According to a second aspect of the present invention, there is provided a method of determining a valve leak comprising the steps of: providing a dialysis machine including a cartridge having a deformable membrane, the cartridge and deformable membrane together defining a membrane pump, the membrane pump defining a flow path arranged to be opened and closed by at least one valve, a measuring device, a comparator; and a signal generator, configuring the measuring device for determining a conductivity value between two points on the flow path of the membrane pump, one point arranged upstream of the at least one valve and the other point arranged downstream of the at least one valve, operating the dialysis machine through a cycle, measuring a conductivity value whenever the at least one valve is closed, continuously monitoring the electrical characteristic throughout the cycle using the comparator, providing an output signal when a conductivity value is indicative of a valve leak condition.

Embodiments of the present invention will now be described, by way of example only, and with references to the accompanying drawings, in which.

DIALYSIS MACHINE

Figure 1:
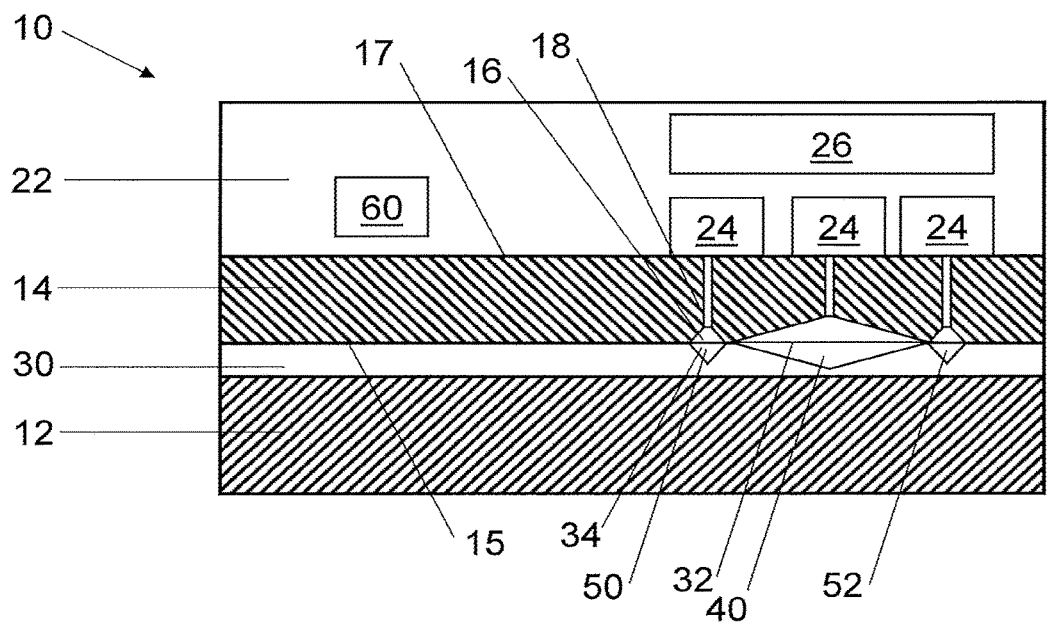
FIG. 1 is a schematic cross-sectional view of a dialysis machine.

A cross section of a dialysis machine 10 is shown schematically in FIG. 1. The dialysis machine 10 has machine body 22. The machine body 22 houses pneumatic actuators 24 and a controller 26. The dialysis machine 10 includes a first platen 12 and a second platen 14. The first and second platens 12, 14 together define a cavity into which a disposable cartridge 30 is received in a known manner.

Figure 2:
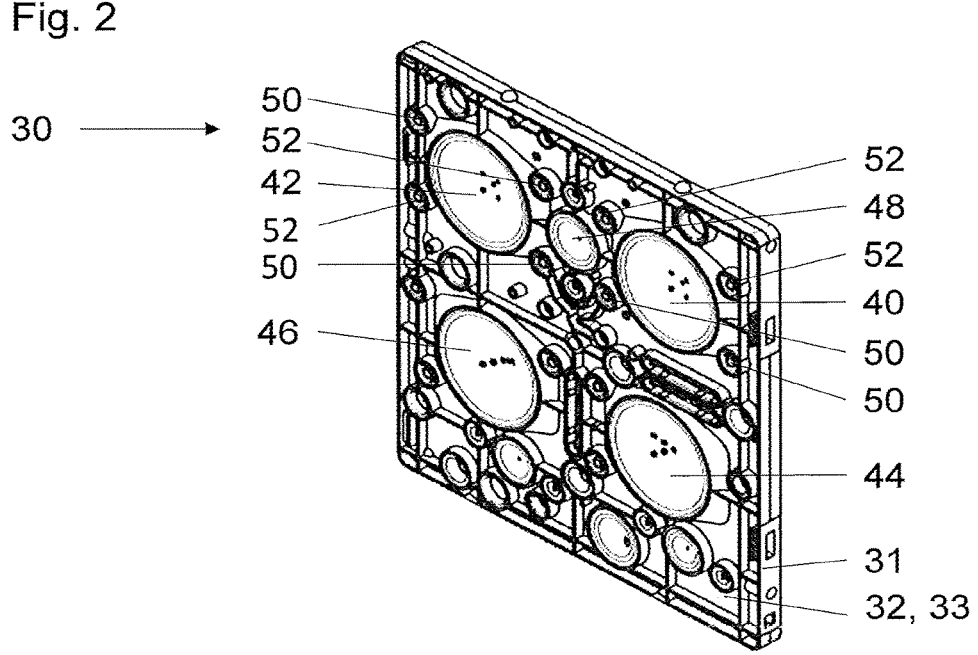
FIG. 2 is a perspective view of a cartridge of the dialysis machine of FIG. 1.
Figure 3:
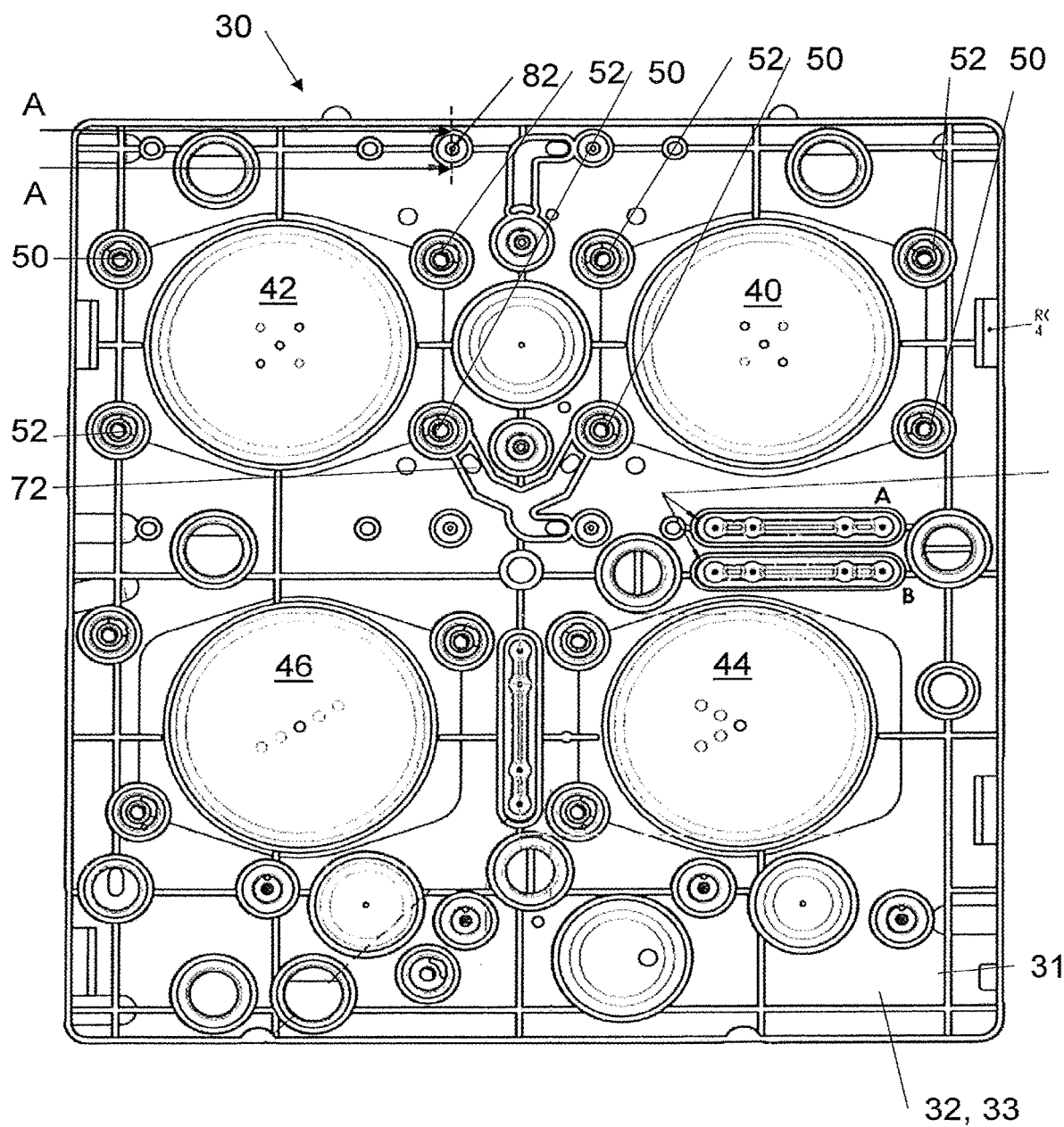
FIG. 3 is a plan view of the cartridge of FIG. 2.

The disposable cartridge 30 (see FIGS. 2 and 3) has a rigid body 31 covered by a flexible membrane 32, providing a machine facing surface 33. The disposable cartridge 30 in part embodies pump chambers and valves. In this case, the chambers are flow balance pump chamber "A" 40, flow balance pump chamber "B" 42, dialysate mixing pump chamber 44, acid mixing pump chamber 46 and ultrafiltration pump chamber 48. The flow balance pump chamber "A" 40 and flow balance pump chamber "B" 42 each have two inlet valves 50 and two outlet valves 52.

The pneumatic operation of each of the chambers 40, 42, 44, 46 and 48 are substantially similar, such that only the flow balance pump chamber "A" 40 shall be described in detail.

Furthermore, the two inlet valves 50 and the two outlet valves 52 are substantially similar, such that only one inlet valve 50 and one outlet valve 52 shall be described in detail.

Referring back to FIG. 1, the flow balance pump chamber "A" 40 and inlet and outlet valves 50, 52 are defined between respective concave cavities 34 formed in the rigid body 31 of the disposable cartridge 30 and the flexible membrane of the cartridge 32. The disposable cartridge 30 defines fluid pathways 28 between the flow balance pump chamber "A" 40 inlet and outlet valves 50, 52.

In use, the disposable cartridge 30 is retained between the first platen 12 on a first side of the disposable cartridge 30 and the second platen 14 on a second side of the disposable cartridge 30. The second platen 14 has a cartridge engaging surface 15 and a non-cartridge engaging surface 17. Cavities 16 are defined within the cartridge engaging surface 15, which correspond to the concave cavities 34 on the disposable cartridge 30. A fluid port 18 is defined in each of the concave cavities 16, fluidly connecting the cartridge engaging surface 15 and the non-cartridge engaging surface 17, of the second platen 14.

The pneumatic actuators 24 are arranged in fluid communication with the second side of the disposable cartridge 30, through the second platen 14 via the fluid ports 18, and hence the machine facing surface 33 of the flexible membrane 32. The pump chambers and valves are operated pneumatically by actuating the flexible membrane 32 using the pneumatic actuators 24 provided in the machine body 22. In an alternative embodiment the pump chambers and valves are operated hydraulically.

Sensing Arrangement

Figure 4:
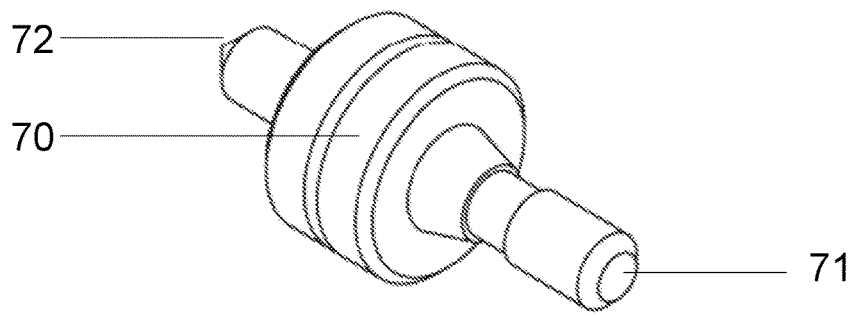
FIG. 4 is a perspective view of a sensing electrode.
Figure 5:
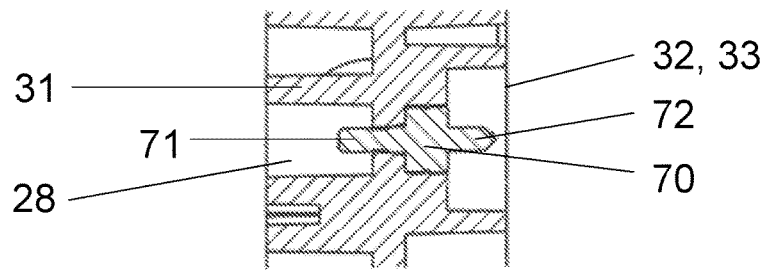
FIG. 5 is a partial cross-sectional view of the cartridge taken at line A-A of FIG. 3.

The pump chambers and valves are provided with sensing arrangements 60, each of which include two sensing electrodes, generally termed 70 (see FIGS. 4 and 5). The sensing electrodes 70 are rotationally symmetrical and are made of a conductive material. The sensing electrodes 70 include a pointed tip 71. The sensing electrodes 70 are mounted in the rigid body 31 of the cartridge 30. The pointed tip 71 is arranged to face the second side of the disposable cartridge 30 and the flexible membrane 32.

Figure 6:
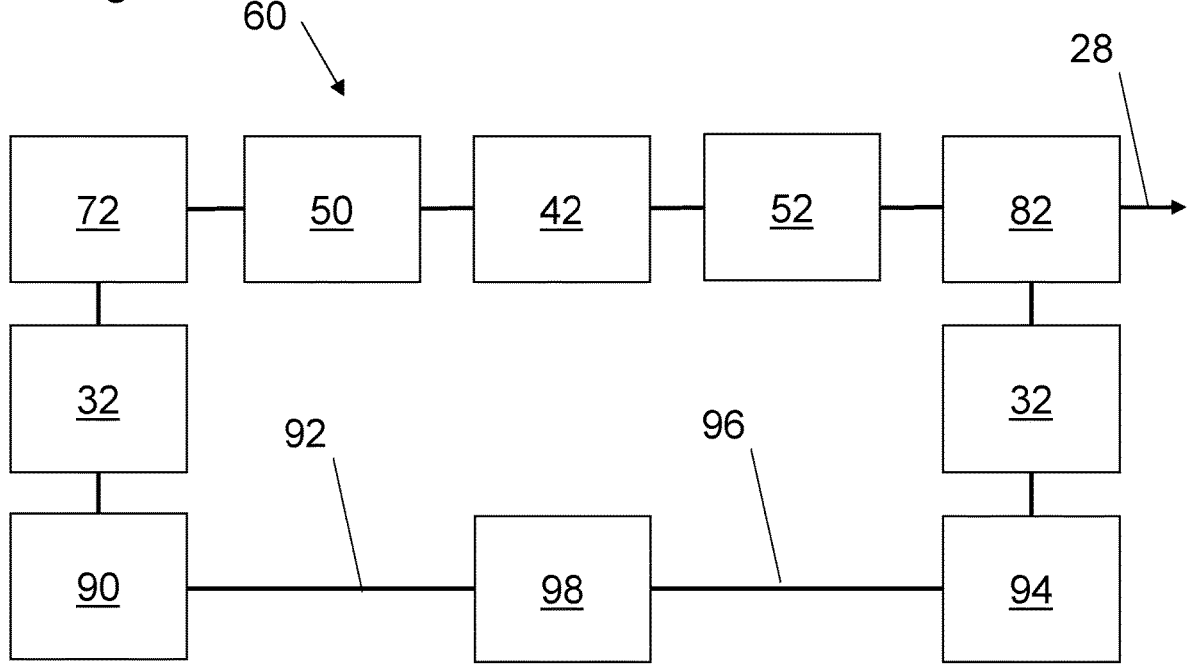
FIG. 6 is a schematic of the fluid flowpath of the sensing arrangement for flow balance pump "B".

The sensing arrangements 60 monitor the flow of fluids through the pump chambers and valves along the various fluid pathways. Referring to FIG. 6, one such fluid pathway is the fluid pathway 28 associated with the flow balance pump chamber "B" 42. As the sensing arrangements 60 are substantially similar, only the sensing arrangement 60 associated with the flow balance pump chamber "B" 42 shall be described in detail.

Flow Balance Pump Chamber "B" Sensing Arrangement

The flow balance pump chamber "B" sensing arrangement 60 is arranged with an inlet valve sensing electrode 72 and outlet valve sensing electrode 82. The inlet valve sensing electrode 72 is fixed to the rigid body 31 of the disposable cartridge 30 with the pointed sensing tip 71 exposed to the fluid flowpath 28 at the entrance to the inlet valve 50. The outlet valve sensing electrode 82 is fixed to the rigid body 31 of the disposable cartridge 30 with the pointed sensing tip 71 exposed to the fluid flowpath 28 at the exit of the outlet valve 52.

Thus the inlet valve sensing electrode 72 is provided upstream of the flow balance pump chamber "B" 42, and outlet valve sensing electrode 82 is provided downstream of the flow balance pump chamber "B" 42.

When the disposable cartridge 30 is loaded into the dialysis machine 10, the inlet valve sensing electrode 72 and outlet valve sensing electrode 82 line up with sprung contacts 90, 94 provided in the second platen 14, sandwiching the flexible membrane 32 therebetween.

The sprung contacts 90, 94 are electrically connected to a processor 98, incorporating a sensor circuit, a comparator and a power source, provided in the machine body 22 via electrical connectors 92, 96 respectively.

Thus inlet valve sensing electrode 72 and outlet valve sensing electrode 82 are electrically connected to the processor 98 through the flexible membrane 32. The inlet valve sensing electrode 72 and outlet valve sensing electrode 82, together with the sprung contacts 90, 94, processor 98 and respective connectors 92, 96 form the sensing arrangement 60.

Valve Function

In use at least one of the inlet valve 50 and the outlet valve 52 will always be closed. That is, there are three modes of operation. In an idle mode, both the inlet valve 50 and the outlet valve 52 are closed. Thus there should be no continuous flowpath between the inlet valve sensing electrode 72 and the outlet valve sensing electrode 82. In a fill mode, the inlet valve 50 is open, and the outlet valve 52 is closed. This allows flow balance pump chamber "B" to be filled. However, there should still be no continuous flowpath between the inlet valve sensing electrode 72 and the outlet valve sensing electrode 82, as the outlet valve is closed. In an empty mode, the inlet valve 50 is closed, and the outlet valve 52 is open. This allows flow balance pump chamber "B" to be emptied. However, there should still be no continuous flowpath between the inlet valve sensing electrode 72 and the outlet valve sensing electrode 82, as the inlet valve 50 is closed. Thus the valve leak system may detect when either of the inlet or outlet valves 50, 52 are leaking using the sensing arrangement 60 shown in FIG. 6.

Valve Leak Detection System, Using Sensing Arrangement

During operation of the dialysis machine 10, the sensing arrangements 60 are used to detect leakage across the pump chambers and valves of the dialysis machine 10.

The sensor circuit of the processor 98, includes an operational amplifier based relaxation oscillator whose frequency is determined by electrical conductance of the fluid path.

In use, an alternating potential difference from the power source is applied across the fluid flowpath 28 by the inlet valve sensing electrode 72. The conductance of the fluid flowpath 28 between the inlet valve 50 and outlet valve 52 of the flow balance pump chamber "B" 42 is measured at the outlet valve sensing electrode 82 by measuring the potential difference detected at the outlet valve sensing electrode 82, as will be described in more detail below. The potential differential provides an indication the conductivity of the fluid flowpath 28. The relaxation oscillator ensures that the sensing arrangement 60 operates with an alternating current with minimal direct current offset. This reduces the galvanic effects on the inlet valve sensing electrode 72 and the outlet valve sensing electrode 82.

The sensor circuit of the processor 98 generates the pulse train from the relaxation oscillator which is sent through the sensing arrangement 60, to output at the processor 98. The output at the processor is a series of pulses. From this series of pulses, a frequency is determined by measuring the time between the pulses, and hence fluid conductivity. This frequency value is known as the valve leak frequency.

The sensing arrangement 60 detects a valve leak in the inlet and outlet valves 50, 52 of the flow balance chamber "B" 42 by performing conductivity checks during operation of the flow balance system. The conductivity along a flow path should not exceed a defined limit if the flow path is interrupted by valves 50, 52. The test is performed once every pump operation. If the inlet or outlet valves 50, 52 fail to close, then the respective pump may draw or expel the fluid associated with that pump the wrong way, which is undesirable. The protective system for this error uses conductivity of the fluid flowpath 28 as a means to determine this failure. Thus in normal operation of the dialysis machine 10, there should never be a conductive path across the whole of the pump, from before the inlet valve 50 to after the outlet valve 52, that has a conductivity of a value equal to or greater than a limit value set by the particular geometry of the cartridge in question. If a conductive path is seen, this may be indicative of one of the valves 50, 52 having failed to close.

Hence the valve leak detection system measures a valve leak frequency value. The valve leak signal is generated by an oscillator and the frequency of the signal is determined by the feedback resistor. The sensing electrodes are connected in parallel to the feedback resistor so that a lower impedance across the valves would cause the total feedback resistor value to decrease, increasing the oscillating frequency.

During normal operation of an exemplary dialysis machine 10 having an exemplary cartridge, the relaxation oscillator is tuned to generate a signal of 6 kHz for a resistance of 10 kOhms across the sensing electrodes The expected detected valve leak frequency value is between 3 kHz and 4 kHz. Should a valve leak frequency value in excess of 6 kHz be detected, a valve leak has occurred.

Membrane Pump Usage Condition Detection

The valve leak detection system described above may be used to determine membrane pump usage and hence disposable cartridge 30 usage.

A partial valve leak (e.g. due to re-used cartridges) is detected when the variation of detected valve leak frequency value within a pumping cycle increases.

A variation in the detected valve leak frequency value is detected by the comparator within the processor 98 measuring the difference between the minimum and maximum valve leak frequency values measured within one pump cycle.

For the normal operation of an exemplary dialysis machine 10 having an exemplary cartridge referred to above, variation of valve leak frequency value is between 200 Hz and 500 Hz. Variations above 1 kHz are considered to be partial valve leak. Thus for this exemplary dialysis machine 10 having an exemplary cartridge, the pre-determined threshold value is a valve leak frequency value difference of 1 kHz.

The value used for the partial valve leak is not the absolute frequency but the variation of the frequency within a pumping cycle. When the valve is partially leaking (e.g. due to re-use of cartridges) the frequency signal is not as stable as it normally is: maximum relative difference of the valve leak frequency value within one pump cycle is more than 1 kHz. Normal expected values of absolute frequency are 3 kHz to 4 kHz with a variation of less than 1 kHz within a pumping cycle.

As the valve leak signal is generated by an oscillator and the frequency of the signal is determined by the feedback resistor, a dynamic threshold value for the valve leak frequency value difference may be used instead of the pre-determined threshold value.

The effects on a disposable cartridge 30 during a dialysis treatment cycle can be represented by a typical test cycle. A typical test cycle includes three main stages, flow balance, ultrafiltration and purge. In the first 30 minutes, the dialysis machine 10 is taken through a flow balance stage of the test cycle. The flow balance stage tests the flow balance valves. During the next 30 minutes, the dialysis machine 10 is taken through an ultrafiltration stage of the test cycle. The ultrafiltration stage tests the ultrafiltration valves. The test cycle is then ended with a purge stage. The purge stage empties the cartridge 30 of all dialysate fluids, and cleans the fluid flow paths with reverse osmosis water.

In order to determine the deterioration rates, the same disposable cartridge 30 is forced through repeated test cycles.

Valve Leak Frequency Profiles

Figure 7:
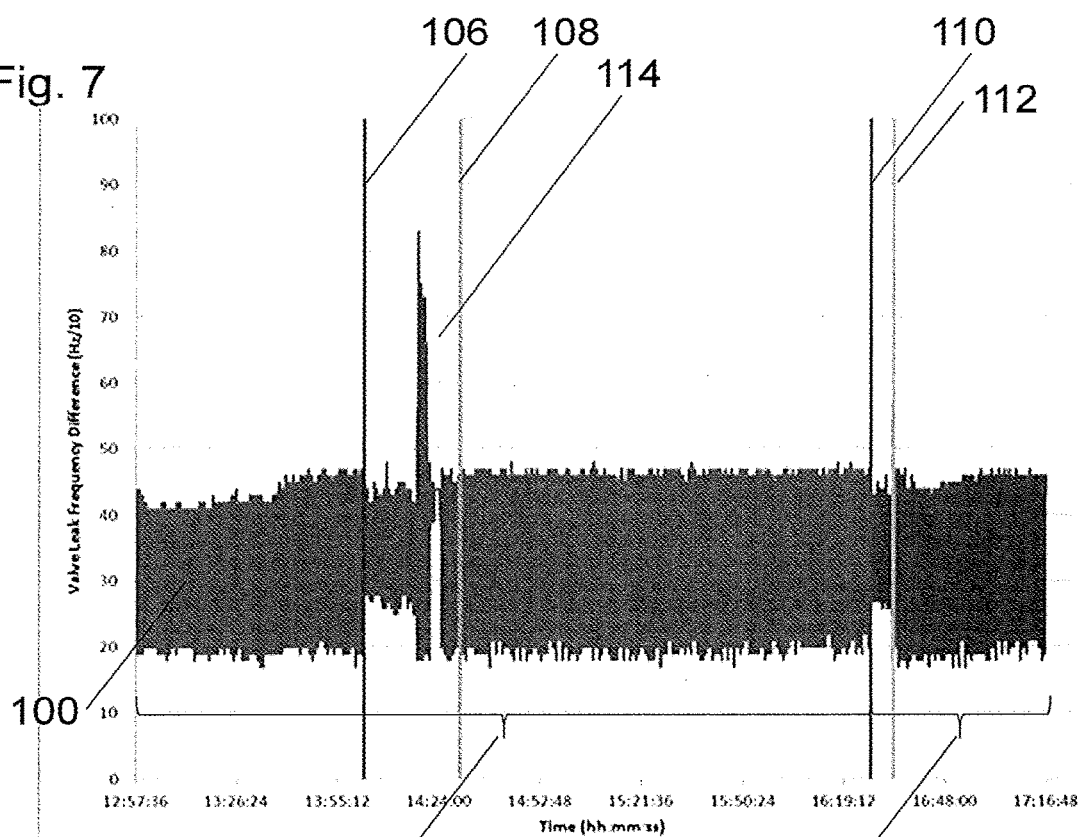
FIG. 7 is a valve leak detection frequency profile of a valve on a cartridge undergoing a typical cycle.

With reference to FIG. 7, a valve leak frequency profile between inlet valve 50 and outlet valve 52, i.e. the fluid flowpath 28 across the flow balance chamber "B" 42, on a disposable cartridge 30 undergoing a typical cycle is shown. The valve leak frequency values are measured every second, a comparison is made between the minimum and maximum valve leak frequency values and plotted as point readings 100 with respect to the Y-axis. A general distribution over the typical cycle time as shown on the X-axis. The first stage of the typical cycle represents the ultrafiltration stage 102 of the cycle, whereas the second stage of the typical cycle represents the flow balance stage 104 of the cycle. During ultrafiltration the blood pump is stopped at 106 and re-started at 108. Similarly, during flow balance, the blood pump is stopped at 110 and re-started at 112.

As can be seen in FIG. 7, whilst the measured valve leak frequency difference varies during a normal treatment session, the magnitude of any single difference value 100 does not exceed 900 Hz. The typical value throughout the cycle for valve leak frequency difference is between 200 Hz and 500 Hz. A spike 114 in the measured valve leak frequency difference value is seen during the ultrafiltration stage 102 of the cycle, the spike 114 reaching a maximum value of approximately 830 Hz.

Figure 8:
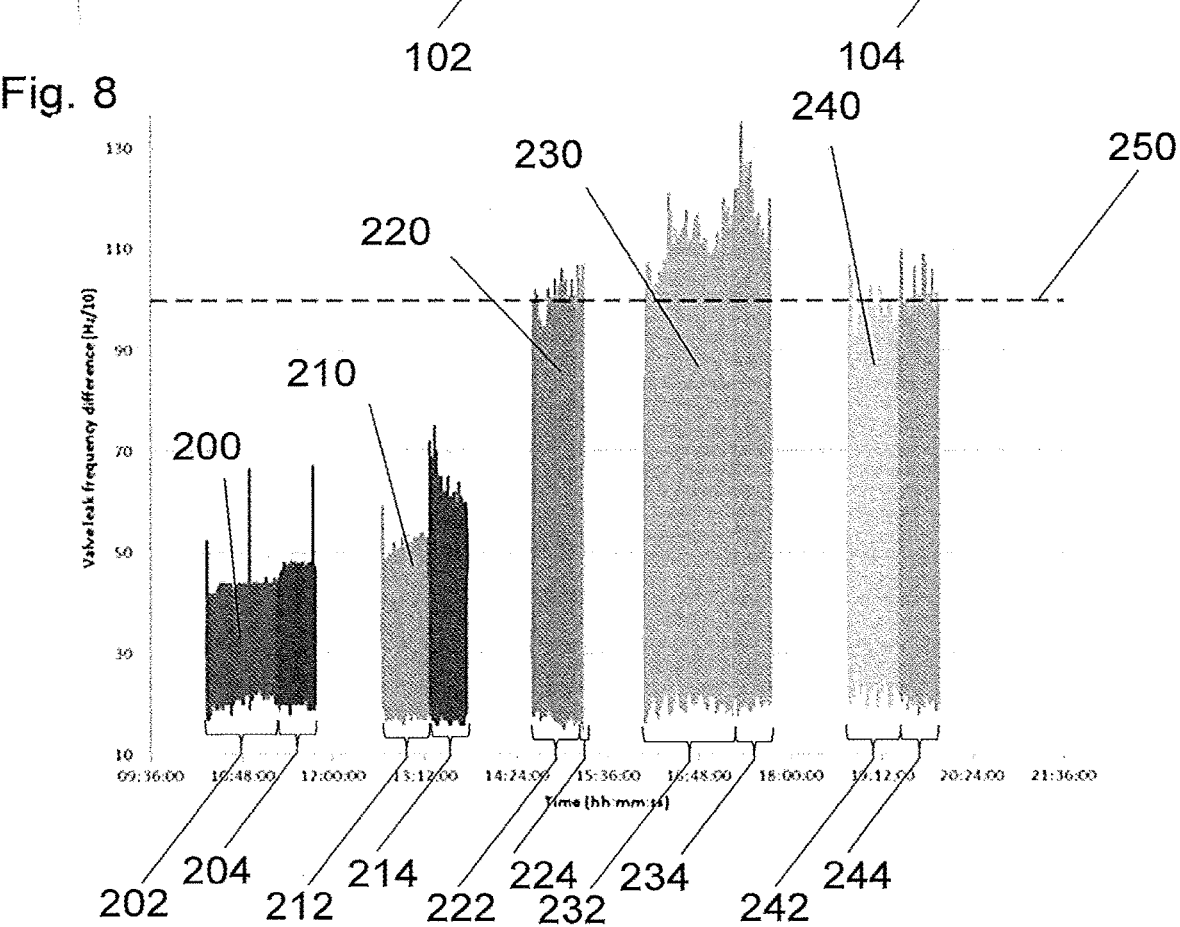
FIG. 8 is a valve leak detection frequency profile of a valve on a cartridge undergoing a sequence of cycles.

With reference to FIG. 8, a disposable cartridge 30 is taken through a series of five typical cycles, numbered as first cycle 200, second cycle 210, third cycle 220, fourth cycle 230 and fifth cycle 240. For each cycle, the valve leak frequency difference values are again plotted as point readings with respect to the Y-axis giving a general distribution over the typical cycle time as shown on the X-axis. Each cycle 200, 210, 220, 230, 240 includes an ultrafiltration stage 202, 212, 222, 232, 242, a flow balance stage 204, 214, 224, 234, 244, and a purge stage. The purge stage follows the flow balance stage 204, 214, 224, 234, 244 for each of the cycles 200, 210, 220, 230, 240 respectively.

The valve leak frequency difference limit 250 is shown as a dashed line at 1000 Hz. The valve leak frequency difference limit 250 may be manipulated depending on the deterioration rates displayed by the cartridge 30.

An increase in the valve leak frequency difference values can be seen from the first cycle 200 to the second cycle 210. This increase in the valve leak frequency difference value represents a deterioration in the flexible membrane of the cartridge. A yet greater increase in the valve leak frequency difference values is seen from the second cycle 210 to the third cycle 220. An alarm is raised during the third cycle 220, as the point readings regularly breach the 1000 Hz valve leak frequency difference limit 250.

Thus FIG. 8 shows that the valve leak frequency difference values increase over several cycles with the method described above, with the rate of deterioration being worse after each re-use, until the flexible membrane is effectively plastically deformed. Further re-use of the same cartridge will thus prevent meaningful treatment sessions, as evidenced in the fourth and fifth cycles 230, 240.

Figure 9:
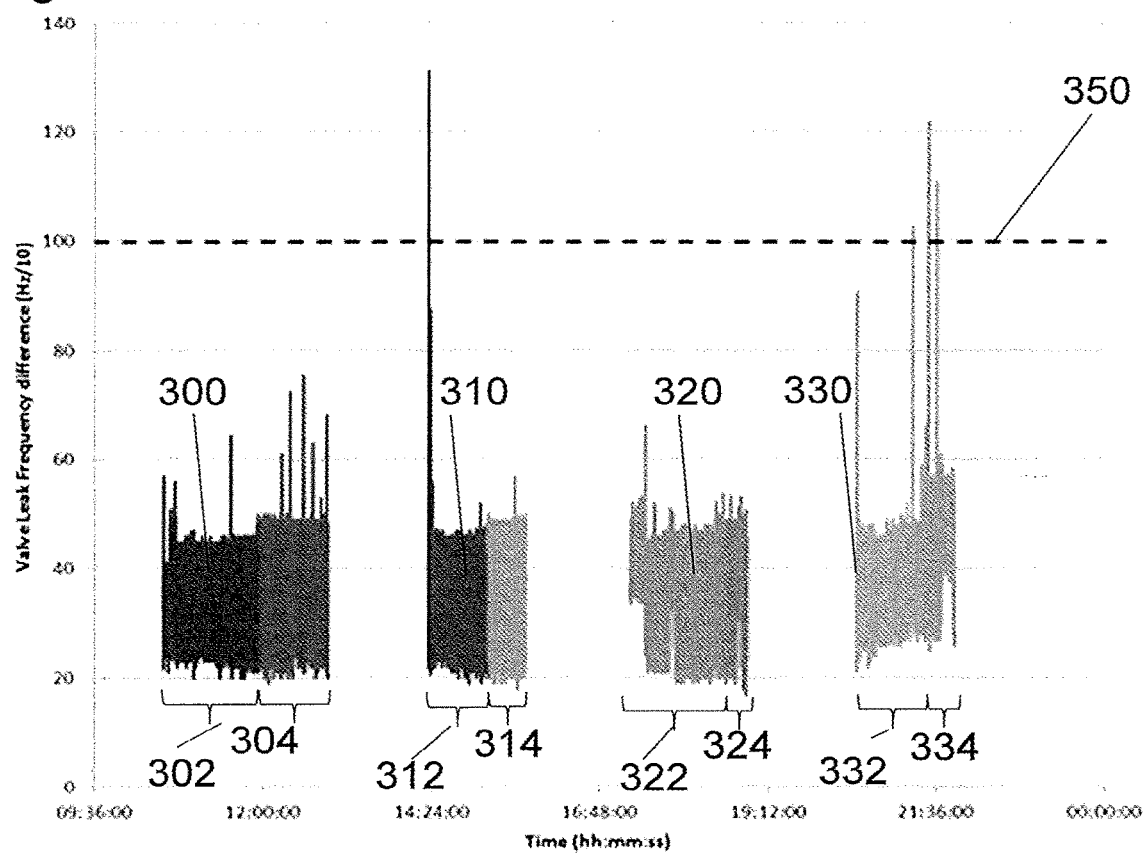
FIG. 9 is a valve leak detection frequency profile of a valve on a cartridge undergoing a sequence of cycles, each cycles omitting the purging stage.

With reference to FIG. 9, a disposable cartridge 30 is taken through a series of five typical cycles, numbered as first cycle 300, second cycle 310, third cycle 320 and fourth cycle 330. For each cycle, the valve leak frequency difference values are again plotted as point readings with respect to the Y-axis giving a general distribution over the typical cycle time as shown on the X-axis. Each cycle 300, 310, 320, 330 includes an ultrafiltration stage 302, 312, 322, 332, and a flow balance stage 304, 314, 324, 334, respectively, however, unlike in FIG. 8, no purge stage. Instead, the dialysis machine 10 is switched off just before the purge stage.

The valve leak frequency difference limit 350 is shown as a dashed line at 1000 Hz.

FIG. 9 shows that the degree of disposable cartridge 30 deterioration is minimal if the purge stage is avoided, thereby allowing an alternative method to re-use the cartridge if necessary. This method of ageing the disposable cartridge 30 does not appear to cause any noticeable deterioration.

Thus the method of determining a disposable cartridge 30 usage condition records the valve leak frequency during the cycle to obtain a characteristic value, and determines the cartridge usage condition based on the characteristic value. The characteristic value may be a single breach of the 1000 Hz valve leak frequency difference limit 250. The characteristic value may be a discreet number of breaches of the 1000 Hz valve leak frequency difference limit 250. The characteristic value may be a decay rate of the valve leak frequency difference following a spike in the valve leak frequency difference. The characteristic value may be the mean, median or modal average valve leak frequency difference during the cycle. The processor 98 may be programmed to monitor any of the preceding characteristic values. On receipt of a characteristic value, the process may send a signal to a graphical user interface, or to an audible or visual alarm to indicate the cartridge usage condition or a signal to prevent activation of the dialysis machine cycle.

Thus the detection system is sensitive enough so that it detects a deterioration of the cartridge membrane before a leak across the valve is established. This allows an operator to prevent use of a disposable cartridge 30 not fit for purpose.

Although the valve leak frequency is described as being measured using the sensing arrangements including sensing electrodes, other sensing arrangements are envisaged. A capacitance probe, which provides a non-contacting fluid flowpath sensing arrangement, is also envisaged, as is an inductance probe which is non-contacting. Other relaxation oscillator types may be used, such as a transistor based relaxation oscillator.

Alternate Sensing Arrangement

Figure 10:
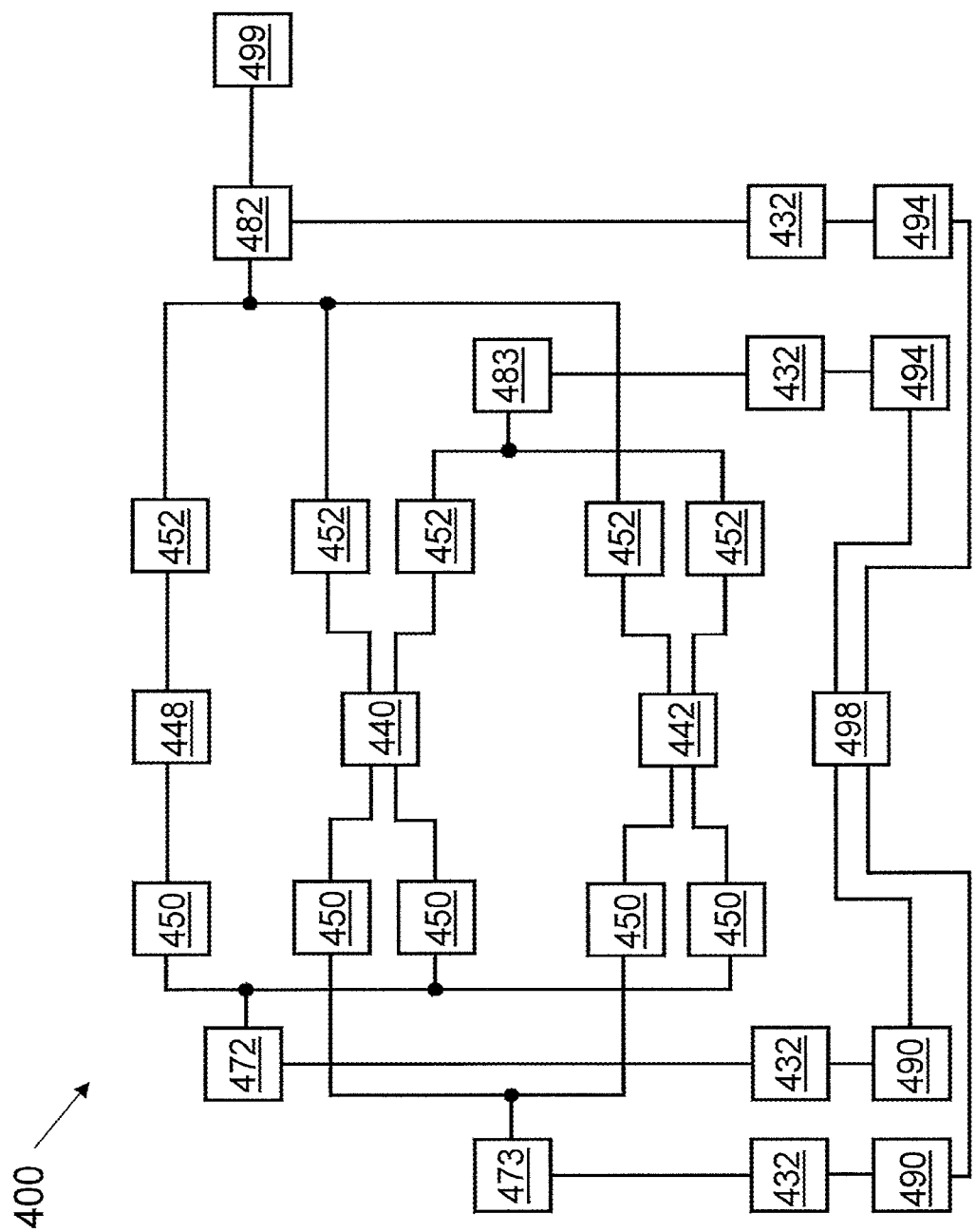
FIG. 10 is a schematic of an alternate sensing arrangement of a valve leak detection system.

FIG. 10 is a schematic of the sensing and valve arrangement of a valve leak detection system 400. In the diagram, dots over crossed lines indicate an electrical connection, whereas lines that cross with no dots are not connected.

The valve leak detection system 400 comprises many of the features as described previously with respect to the dialysis machine 10 and sensing arrangement 60 of FIGS. 1 to 6. Similar features have been given similar reference numerals, prefixed by "4" to indicate that they are being described with respect to the valve leak detection system 400.

The valve leak detection system 400 comprises a flow balance pump chamber "A", 440, a flow balance pump chamber "B", 442, and an ultrafiltration pump chamber 448. As with the sensing arrangement 60, these chambers 440, 442, 448 are embodied in part on a disposable cartridge 30. Each of the chambers 440, 442 have two inlet valves 450 and two outlet valves 452. The ultrafiltration pump chamber 448 has a single inlet valve 450 and a single outlet valve 452.

A first inlet sensing electrode 472 is arranged on the fluid pathway upstream of the ultrafiltration inlet valve, the first flow balance chamber "A" inlet valve and the first flow balance chamber "B" inlet valve 450. A second inlet sensing electrode 473 is arranged on the fluid pathway upstream of the second flow balance chamber "A" inlet valve 450 and the second flow balance chamber "B" inlet valve 450.

Similarly, a first outlet sensing electrode 482 is arranged on the fluid pathway downstream of the ultrafiltration outlet valve, the first flow balance chamber "A" outlet valve and the first flow balance chamber "B" outlet valve 452. A second outlet sensing electrode 483 is arranged on the fluid pathway downstream of the second flow balance chamber "A" outlet valve 452 and the second flow balance chamber "B" outlet valve 452.

Each of these sensing electrodes 472, 473, 482, 483 are electrically connected to respective spring contacts 490, 494 through a portion of the flexible membrane 432.

The spring contacts 490, 494 are electrically connected to a controller 498. The controller comprises a comparator 405, a signal generator 406 and a processor 408 as will be described in more detail below. The first outlet sensing electrode 482 is connected to Earth via a drain line 499.

Valve Leak Detection System Using Alternate Sensing Arrangement

Figure 11:
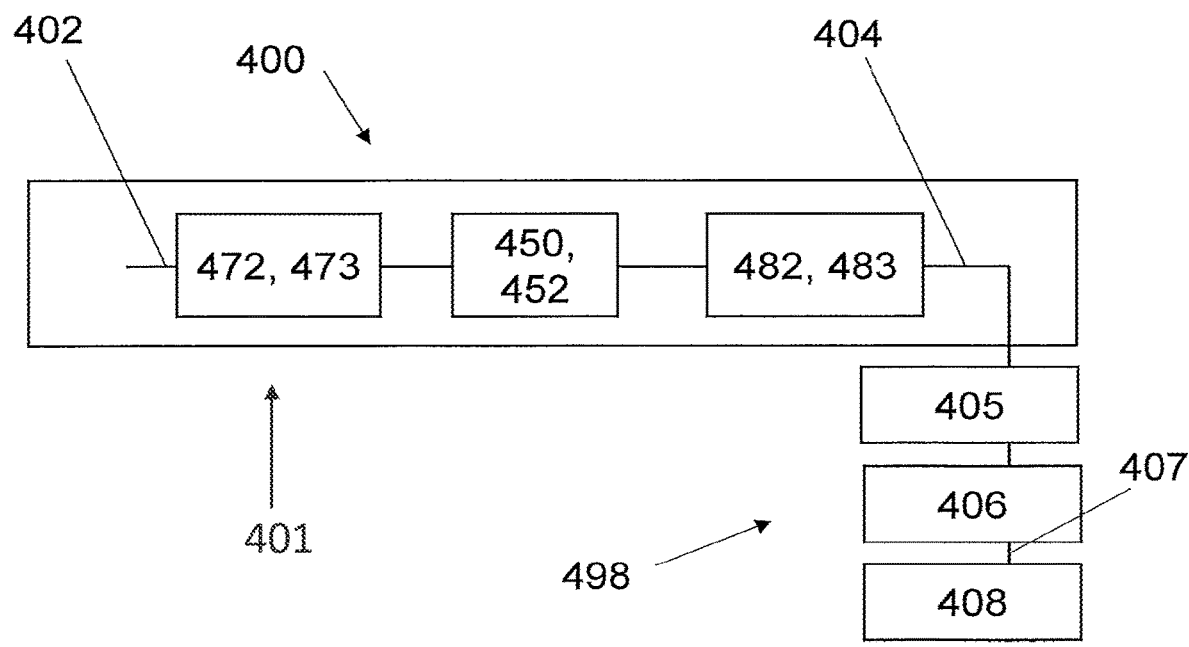
FIG. 11 is a schematic of use of an alternate sensing arrangement of a valve leak detection system.

Use of the valve leak detection system 400 is shown schematically in FIG. 11.

The measuring device 401 is configured to determine a conductivity value between two points on the flow path of the membrane pump. A first point is arranged upstream of the inlet valves 450 and a second point is arranged downstream of the outlet valves 452. The measuring device delivers an emitted signal 402 at a certain frequency via the first and second inlet sensing electrodes 472, 473 whilst the valves 450,452 are closed. The emitted signal 402 is detected at the first and second outlet sensing electrodes 482, 483 as a received signal 404.

The comparator 405 is configured to monitor the conductivity value, the signal generator 406 is arranged to provide an output signal 407 accordingly, and the processor 408 is arranged to receive the output signal 407.

Valve Leak Detection Frequency Profiles

Figure 12:
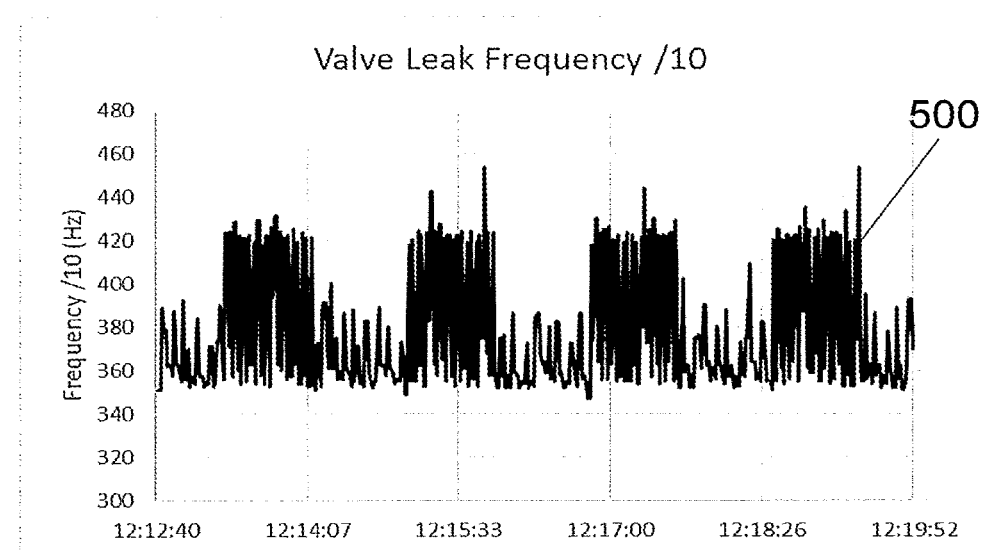
FIG. 12 is a valve leak detection frequency profile of a valve on a leaking cartridge undergoing a typical cycle.

With reference to FIG. 12, a valve leak frequency profile between all inlet valves 450 and all outlet valves 452, i.e. the fluid flowpaths across flow balance chamber "A" 440, flow balance chamber "B" 442 and ultrafiltration pump chamber 448, on a leaking cartridge 30 undergoing a typical cycle is shown.

The valve leak frequency values are measured every second, and plotted as point readings 500 with respect to the Y-axis. A general distribution over the typical cycle time as shown on the X-axis.

In a typical cycle, the valves 450, 452 controlling flow balance chamber "A" 440, flow balance chamber "B" 442 and ultrafiltration pump chamber 448 are operated in discrete patterns. Thus only certain pre-determined fluid pathways will have been opened and closed, in the time period immediately preceding the measurement of valve leak frequency. Thus the valve leak frequency profile of FIG. 12 showing the point reading 500 displays alternate fluid pathways over the typical cycle time.

The raw valve leak frequency measurements are taken from a system where at least one of the valves 450, 452 is partially leaking.

A variation in the detected valve leak frequency value is detected by the comparator 405 within the processor 408 measuring the difference between the minimum and maximum valve leak frequency values measured within one pump cycle.

Figure 13:
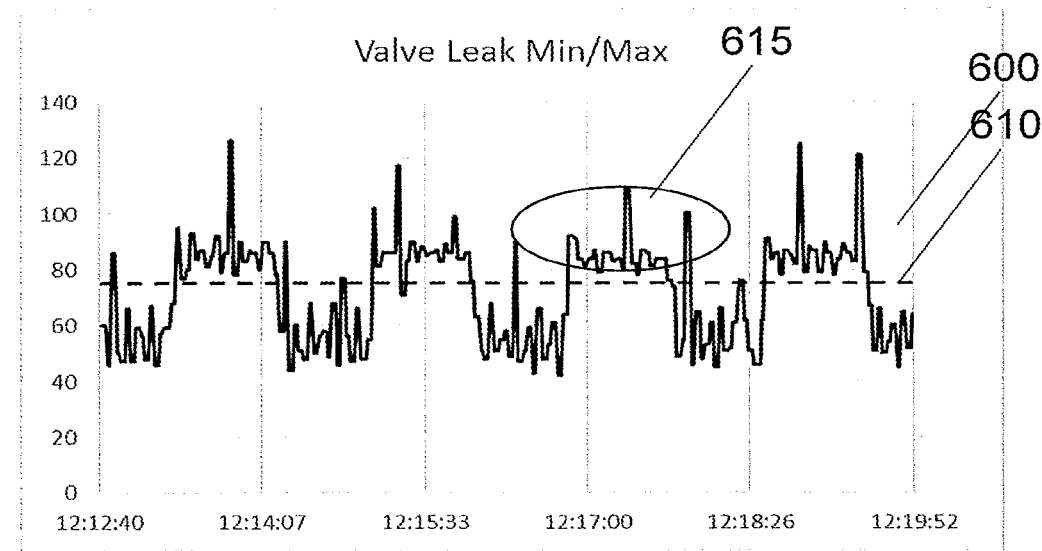
FIG. 13 is a processed valve leak detection frequency profile of FIG. 12.

By detecting the variation, the oscillatory nature of the data is removed. This variation data is shown in FIG. 13, as a plot of processed point readings 600. The processing can be seen to improve the consistency of the values from FIG. 12. Also shown on FIG. 13 is dashed line which represents a pre-determined threshold 610. The predetermined threshold 610 is set at a change of 750 Hz.

The processor 408 is configured to count the number of processed points readings 600 of valve leak system that are over the pre-determined threshold 610. It can be seen from FIG. 13 that a large proportion of the processed point readings 600 taken are above this limit. These indicate that a leaking valve is present on a fluid pathway being opened and closed. For example region 615 shows a series of processed point values 600 above the threshold limit 610.

Figure 14:
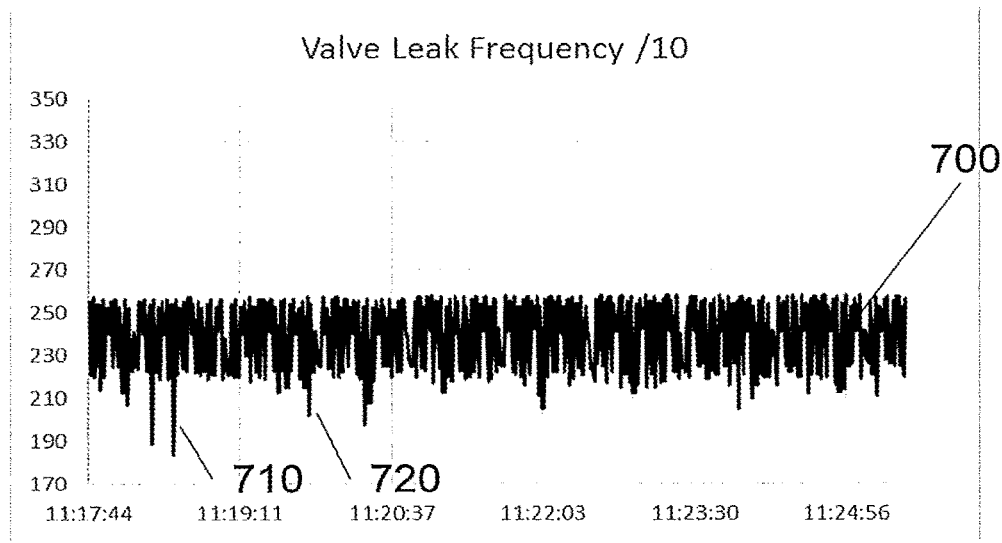
FIG. 14 is a valve leak detection frequency profile of a valve on a non-leaking cartridge undergoing a typical cycle.

FIG. 14 shows a valve leak frequency profile between all inlet valves 450 and all outlet valves 452 on a cartridge 30 without leaking valves. The valve leak frequency values are measured every second, and plotted as point readings 700 with respect to the Y-axis. A general distribution over the typical cycle time as shown on the X-axis.

Figure 15:
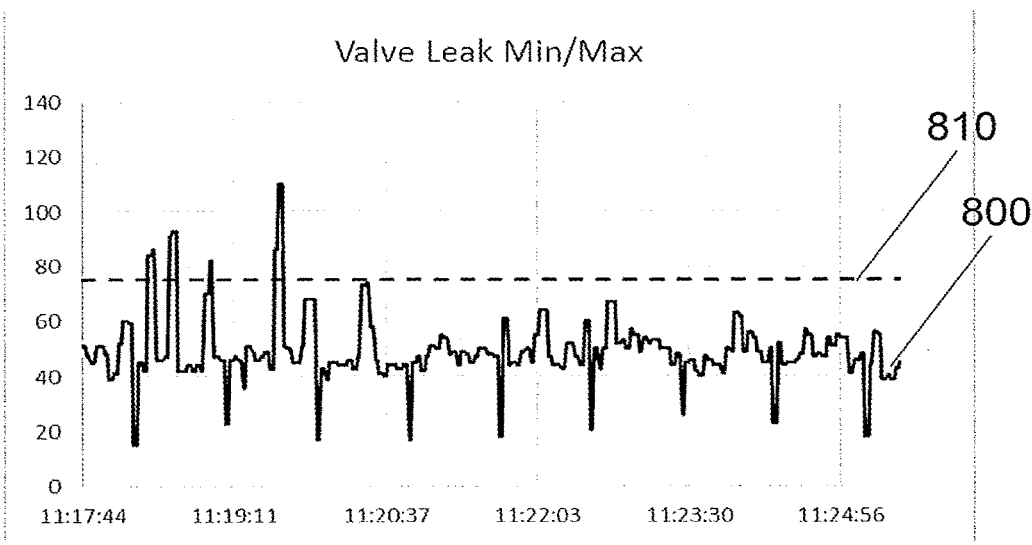
FIG. 15 is a processed valve leak detection frequency profile of FIG. 14.

The reason there are discrepancy spikes, such as at 710 and 720, is due to environmental factors (such as air in the system) causing troughs in the frequency responses for short periods of time. These point readings 700 are initially processed by the comparator 405. The variation in the detected valve leak frequency value is detected by the comparator 405 within the processor 408 measuring the difference between the minimum and maximum valve leak frequency valves measured within one pump cycle. This variation data is shown in FIG. 15, as a plot of processed point readings 800. In FIG. 15, there are some peaks that come as a result of the troughs in the unprocessed readings shown in FIG. 14. The same predetermined threshold 810 of 750 Hz is included in FIG. 15, and it can be seen that although some peaks do reach higher than the threshold, they are not nearly as frequent as in a real valve leak (shown in FIG. 13). However there are no longer any regions having a processed point readings above the threshold limit, like region 615 on FIG. 13.

Figure 16:
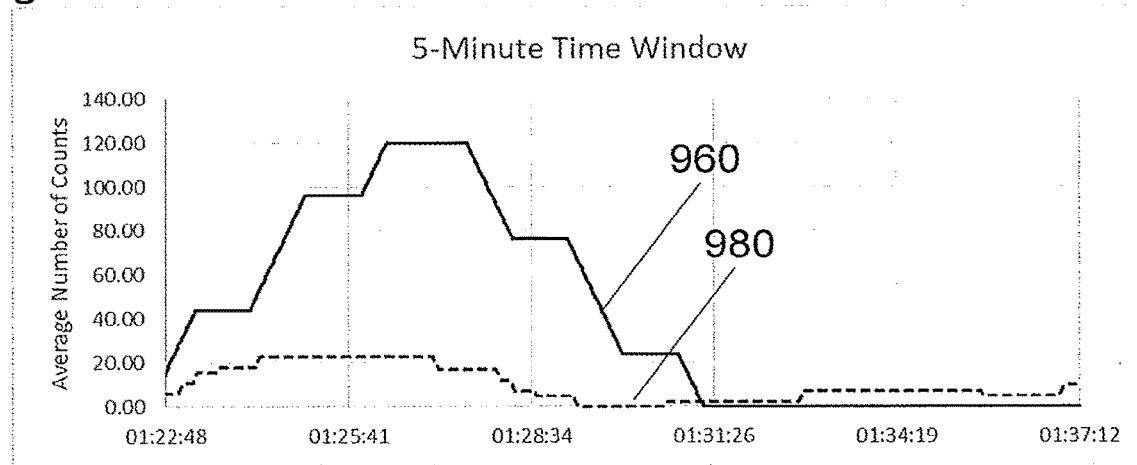
FIG. 16 is a plot of the number of processed readings above a predetermined threshold value for the processed readings of FIGS. 13 and 15.

FIG. 16 demonstrates the cumulative effect of the comparator 405 continuously monitoring the variation in the conductivity value. The variation in the conductivity value is monitored for a set period of time using the moving time window of the valve leak detection system 400. The number of measurements above the predetermined threshold during a 5 minute window is shown for the processed data for a real valve leak 960 (from FIG. 13) and for no valve leak but with environmental factors 980 (from FIG. 15).

The processor 408 will take each reading higher than the threshold over a moving time window before the time of each measurement. FIG. 16 shows a graph of a 5-minute time window of counts found in the two examples shown in the FIGS. 13 and 15. It can be seen that the count numbers are much higher in the case of the real valve leak as compared to the effect of air in the system. There is a large band in between these cases where an alarm limit may be positioned in order to raise an alarm when a real partial valve leak occurs while avoiding unwanted alarms due to the effects of air and other environmental conditions. For example between 40 and 120 on FIG. 16. The determination of the alarm limit can be thus based on the required sensitivity of time valve leak versus environmental factors.

Whilst the valve leak detection system has been described with respect to valve leak detection system 400, the same processing may be applied to the sensing arrangement 60 described above.

In exemplary embodiments, the moving time window may be set anywhere between 1 minute and 60 minutes, or anywhere between 2 minutes and 15 minutes, depending upon the specific dialysis machine and treatment cycle.

Figure 17:
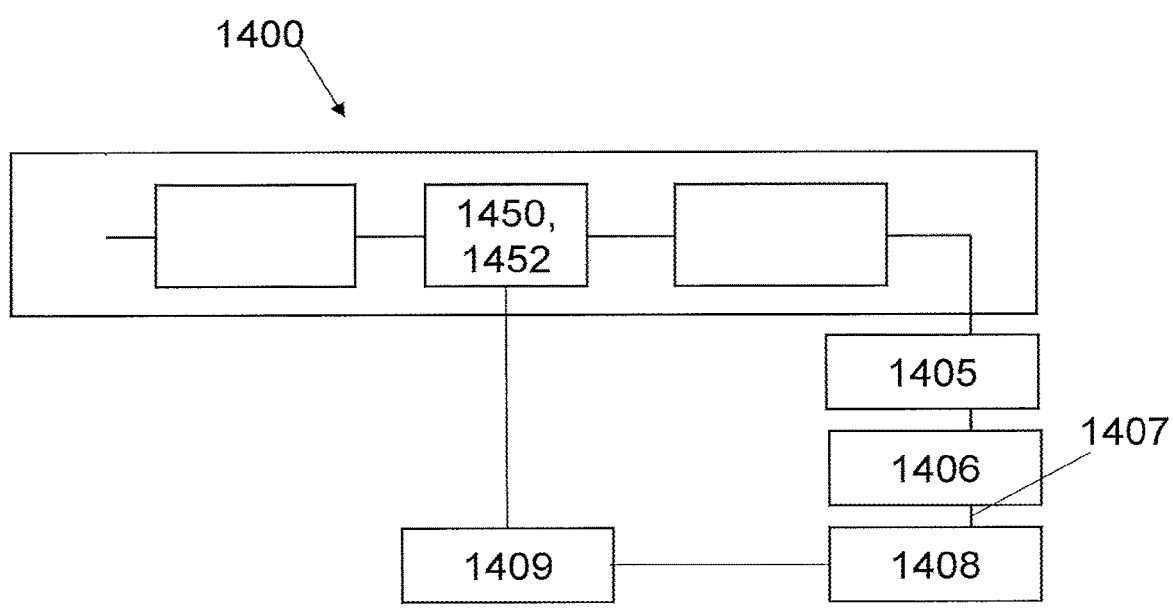
FIG. 17 is a schematic of an alternate sensing arrangement of a valve leak detection system.

An alternate valve leak detection system 1400 is shown schematically in FIG. 17.

The valve leak detection system 1400 is substantially the same as valve leak detection system 400 of FIG. 11, such that only the main differences shall be described in detail. Similar features are given similar reference numbers, prefixed with a '1' to indicate that those features relate to valve leak detection system 1400.

Valve leak detection system 1400 includes valve actuator 1409, which is responsible for opening and closing inlet valve 1450 and outlet valve 1452. The valve actuator 1409 is electrically connected to processor 1408 such that processor 1408 can determine when the inlet and outlet valves 1450, 1452 are open and closed.

As with valve leak detection system 1400, the comparator 1405 is configured to monitor the conductivity value, the signal generator 1406 is arranged to provide an output signal 1407 accordingly, and the processor 1408 is arranged to receive the output signal 1407.

In use, the processor 1408 is configured to take each reading higher than the threshold over a predetermined window that is set according to a number of valve operations. A valve operations is understood to mean a valve changing from an open state to a closed state.

In exemplary embodiments, the set number of valve operations may be 10 inlet valve 1450 operations and 10 outlet valve 1452 operations.

In an alternative exemplary embodiment, the set number of valve operations may be 100 inlet valve 1450 operations and 100 outlet valve 1452 operations.

In an alternate arrangement, the valve leak detection system 1400 may operate the processor 1408 to take each reading higher than the threshold over a predetermined window that is a combination of a set number of valve operations and a moving time window.

The invention claimed is:

1. A valve leak detection system comprising:
    a disposable cartridge including a rigid frame covered by
        a membrane, the cartridge configured to be received in
        a dialysis machine and includes:
        at least one membrane valve;
        a membrane pump;
        a flow path associated with the membrane pump and
            covered by the membrane, the flow path configured
            to be opened and closed by the at least one membrane valve;

a measuring device comprising at least a first electrode and a second electrode;
a processor configured to at least operate as a comparator; and
a signal generator,
wherein:
the measuring device is configured to determine a conductivity value across the at least one membrane valve between a first point and a second point on the flow path of the membrane pump when the at least one membrane valve is closed,
the first point being arranged upstream of the at least one membrane valve and the second point being arranged downstream of the at least one membrane valve,
the first electrode being positioned along the flow path at the first point and the second electrode being positioned along the flow path at the second point;
each electrode comprises a tip and is mounted in the frame of the cartridge such that the end of each respective tip is exposed to the fluid path;
the comparator is configured to continuously monitor the conductivity value, and
the signal generator is configured to provide an output signal when the conductivity value is indicative of a valve leak condition for a set number of measurements within a predetermined window.

2. The valve leak detection system of claim 1, wherein the predetermined window is a time window.

3. The valve leak detection system of claim 2, wherein the time window is a moving time window.

4. The valve leak detection system of claim 1, wherein the predetermined window is a set number of valve operations.

5. The valve leak detection system of claim 4, wherein the predetermined window is a combination of a moving time window and the set number of valve operations.

6. The valve leak detection system of claim 1, wherein the conductivity value is determined by taking measurements of the frequency of an oscillating voltage applied across the measuring device.

7. The valve leak detection system of claim 6, wherein the comparator further measures the difference between the minimum and maximum conductivity values measured within a single pump cycle of the dialysis system to detect one or more variations in the conductivity value.

8. The valve leak detection system of claim 7, wherein the comparator further compares the variation in the conductivity value with a predetermined threshold value.

9. The valve leak detection system of claim 8, wherein the output signal is provided when the variation in the conductivity value is above the threshold value.

10. The valve leak detection system of claim 7, wherein the comparator further compares the variation in the conductivity value with a dynamic threshold value.

11. The valve leak detection system of claim 1, wherein the output signal is stored in the processor.

12. The valve leak detection system of claim 1, wherein:
the at least one membrane valve comprises two membrane valves;
the membrane pump is arranged to be opened and closed by the two membrane valves, a first membrane valve arranged upstream of the membrane pump and a second membrane valve arranged downstream of the membrane pump, and
the first point is arranged upstream of the first membrane valve and the second point is arranged downstream of the second membrane valve.

13. The system of claim 7, wherein the single pump cycle comprises a priming stage, a treatment stage, and a purge stage.

14. A method of detecting a valve leak comprising the steps of:
providing a dialysis machine including:
a cartridge having a deformable membrane and a rigid frame, the cartridge and deformable membrane together defining a membrane pump, the membrane pump including a flow path covered by the membrane and arranged to be opened and closed by at least one membrane valve,
a measuring device comprising a first electrode and a second electrode, the first electrode being positioned at a first point along the flow path and the second electrode being positioned at a second point along the flow path, each electrode comprises a tip and is mounted in the frame of the cartridge such that the end of each respective tip is exposed to the fluid path,
a processor configured to operate as a comparator, and
a signal generator,
configuring the measuring device for determining a conductivity value via the electrodes between the first point and the second point on the flow path, the first point arranged upstream of the at least one membrane valve and the second point arranged downstream of the at least one membrane valve,
operating the dialysis machine through a cycle, measuring the conductivity value across the membrane valve whenever the at least one membrane valve is closed, and
continuously monitoring the conductivity value throughout the cycle using the comparator, and using the signal generator to provide an output signal when the conductivity value is indicative of a valve leak condition for a set number of measurements within a predetermined window.

15. A method of detecting a valve leak according to claim 14, wherein the predetermined window is defined as a time window, a moving time window, a set number of membrane valve operations or a combination of a moving time window and a set number of membrane valve operations.

* * * * *